March 9, 1976 W. A. WARRINER Plant Pat. 3,838
ROSE PLANT
Filed Dec. 13, 1974
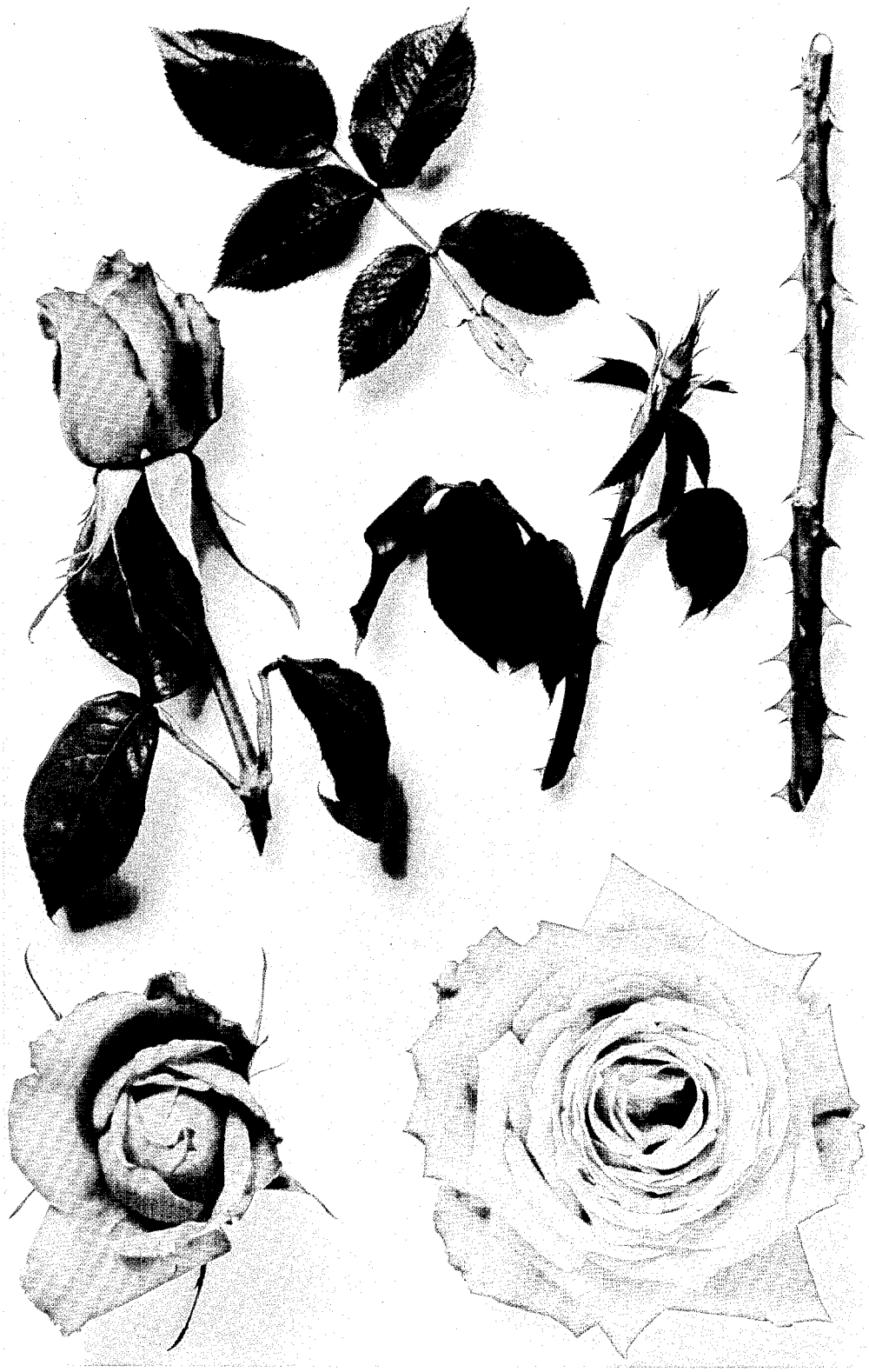

United States Patent

Plant Pat. 3,838

Patented Mar. 9, 1976

3,838

ROSE PLANT

William A. Warriner, Tustin, Calif., assignor to Jackson & Perkins Company, Medford, Oreg.

Filed Dec. 13, 1974, Ser. No. 532,709

Int. Cl. A01h *5/00*

U.S. Cl. Plt.—20 1 Claim

The present invention relates to a new and distinct cultivar of rose plant of the hybrid tea class which was originated by me by crossing an unnamed seedling cultivar by the cutlivar Bob Hope, U.S. Plant Pat. 2,734.

The primary objective of this breeding was to produce a new rose cultivar of very vigorous character, bearing large, fragrant crimson or near crimson blooms.

This objective was substantially achieved along with other desirable improvements as evidenced by the following unique combinations of characteristics which are outstanding in the new cultivar and which distinguish it from its parents as well as from all other cultivars of which I am aware:

1. A very vigorous, upright habit of growth.
2. Large double, heavy textured flowers ranging from Currant Red (W) in the bud to Crimson (W) in the open form.
3. Large, leathery foliage.
4. Strong fragrance.
5. An average resistance to rose powdery mildew.

Asexual reproduction of this new cultivar by budding as performed at Wasco, Calif., proves that the foregoing characteristics and distinctions reproduce true to form and are established and transmitted through succeeding propagations.

The accompanying illustration shows typical specimens of the vegetative growth and flowers of this new cultivar in different states of development, depicted in color as nearly true as it is reasonably possible to make the same in a color illustration of this character.

The following is a detailed description of my new rose variety wtih color terminology in accordance with *Wilson's Horticultural Color Chart,* except where ordinary dictionary significance of color is indicated.

Parentage: Seedling.
- *Seed Parent.*—(Pink Peace x Happiness).
- *Pollen Parent.*—Bob Hope, U.S. Plant Pat. 2,734.

Classification:
- *Botanical.*—Rosa hybrid.
- *Commercial.*—Hybrid tea.

FLOWER

Observations were made at Irvine, Calif., in October.

Blooming habit: Recurrent, continuous.

Bud:
- *Size.*—1⅛" to 1¼" when petals start to unfurl.
- *Form.*—Pointed, ovoid.
- *Color.*—When sepals first divide—near Currant Red (821). When half blown; upper side of petals near Crimson (22) with shading in iregular areas of Cherry (722/3); lower side of petals near Crimson (22).
- *Sepals.—Color:* Outer surface Scheeles Green (860/3). Inner surface midrib area, near Garnet Brown (00918/3), outer edges Scheeles Green (860/2) all covered with moderate white tomentum. Three appendaged sepals normally appendaged. Two unappendaged sepals hairy edged.
- *Receptacle.—Color*: Scheeles Green (860/3). Shape: Funnel. Size: Large, broad. Surface: Smooth.
- *Peduncle.*—Length: Medium. Surface: Prickly. Color: Bronzy. Strength: Stiff, erect, heavy.
- *Opening.*—Petals fold outwardly from center, ball like form.

Bloom:
- *Size.*—Large. Average open size 6".
- *Borne.*—Singly, occasionally several together.
- *Stems.*—Long, strong.
- *Form.*—When first open, high centered. Permanence—flatens, outer petal edges slightly curled.
- *Petalage.*—Number of petals under normal conditions 50–60.
- *Color.*—Center of flower: Upper side of petals Crimson (22). Reverse side of petals Crimson (22/1). Base of petals Canary Yellow (2). General tonality from a distance Crimson.
- *Discoloration.*—General tonality at end of first day—no change. Third day—lightens to Crimson (22/1) or (22/2).

Petals:
- *Texture.*—Thick.
- *Shape.*—Round.
- *Form.*—Tips slightly recurved.
- *Arrangement.*—Imbricated. Petaloids in center—few.
- *Persistence.*—Drop off cleanly.
- *Fragrance.*—Strong.
- *Lastingness.*—On the plant—long. As cut flower—long.

Reproductive parts:
- *Stamens, Anthers.*—Large. Color—Lemon Yellow (4). Arrangement—regular around styles.
- *Filaments (Threads).*—Color—Vermilion (18).
- *Pollen.*—Gold Yellow.
- *Styles.—Color*—lower portion White, upper third (approximately) Crimson.
- *Stigmas.*—Color—Yellow.

PLANT

Form: Bush.

Growth: Vigorous, upright, branching.

Foliage: Number of leaflets on normal mid-stem leaves 5.
- *Size.*—Large.
- *Quantity.*—Normal.
- *Color.*—New foliage: Garnet Brown (00918). Old foliage: Spinach Green (0960).
- *Shape.*—Oval.
- *Texture.*—Leathery.
- *Edge.*—Serrated.
- *Serration.*—Single, small.
- *Petiole (rachis).*—Color — green. Underside — prickles.
- *Stipules.*—Long, serrated.
- *Disease Resistance.*—Normally resistant to mildew under normal growing conditions at Irvine, Calif.

Wood:
- *New Wood.*—Color—Garnet Brown (00918). Bark—smooth.
- *Old Wood.*—Color—Green with shadings of Garnet Brown (00918/3). Bark-smooth.

Prickles:

*Quantity.*—On main stalks from base—ordinary. On laterals from stalk—ordinary.

*Form.*—Broad based, long, hooked downwardly.

*Color When Young.*—Brown.

*Position.*—Irregular.

Small prickles:

*Quantity.*—On main stalks—few. On laterals—few.

*Color.*—Brown.

I claim:

1. A new and distinct cultivar of rose plant of the hybrid tea class, substantially as herein shown and described, characterized particularly as to novelty by the unique combination of its vigorous, upright growth, Currant Red buds, Crimson open flowers of 50–60 petals, very strong fragrance, large leathery foliage.

No references cited.

ROBERT E. BAGWILL, Primary Examiner